(12) United States Patent
Login

(10) Patent No.: US 9,023,976 B2
(45) Date of Patent: May 5, 2015

(54) AMIDE-IMIDE COMPOUNDS AND THEIR CORRESPONDING POLYMERS

(71) Applicant: Robert Bernard Login, Bothell, WA (US)

(72) Inventor: Robert Bernard Login, Bothell, WA (US)

( * ) Notice: Subject to any disclaimer, the term of this patent is extended or adjusted under 35 U.S.C. 154(b) by 55 days.

(21) Appl. No.: 13/875,272

(22) Filed: May 1, 2013

(65) Prior Publication Data

US 2014/0329986 A1 Nov. 6, 2014

(51) Int. Cl.
*C08G 73/10* (2006.01)
*C08G 73/14* (2006.01)
*C07D 471/10* (2006.01)

(52) U.S. Cl.
CPC .............. *C08G 73/14* (2013.01); *C07D 471/10* (2013.01); *C08G 73/10* (2013.01)

(58) Field of Classification Search
USPC ........... 524/306, 314, 315; 528/188, 350, 354
See application file for complete search history.

(56) References Cited

U.S. PATENT DOCUMENTS

| | | | |
|---|---|---|---|
| 2,386,454 A | 10/1945 | Frosch | |
| 2,396,626 A | 3/1946 | Wiest | |
| 2,463,977 A | 3/1949 | Kropa | |
| 2,502,576 A * | 4/1950 | Lincoln et al. | 528/350 |
| 2,806,822 A | 9/1957 | Dayton | |
| 4,209,607 A | 6/1980 | Shalaby et al. | |
| 4,343,931 A | 8/1982 | Barrows | |
| 4,380,622 A | 4/1983 | Chiba et al. | |
| 4,483,975 A | 11/1984 | deJong | |
| 4,536,563 A | 8/1985 | Okitsu | |
| 4,602,061 A | 7/1986 | Akkerman | |
| 4,604,449 A | 8/1986 | Jackson | |
| 4,855,397 A | 8/1989 | Barbee | |
| 5,347,043 A | 9/1994 | Sabahi | |
| 5,350,875 A | 9/1994 | Kumar et al. | |
| 5,399,279 A | 3/1995 | Sabahi | |
| 5,430,177 A | 7/1995 | Sabahi | |
| 5,536,872 A | 7/1996 | Sabahi et al. | |
| 5,538,661 A | 7/1996 | Dawson | |
| 5,569,779 A | 10/1996 | Sabahi | |
| 5,644,020 A | 7/1997 | Timmermann | |
| 5,683,618 A | 11/1997 | Sabahi | |
| 5,902,875 A | 5/1999 | Roby | |
| 6,268,465 B1 | 7/2001 | Chomiakow | |
| 7,166,680 B2 | 1/2007 | DesNoyer | |
| 7,196,127 B2 | 3/2007 | Lai | |
| 7,396,429 B2 | 7/2008 | Beckley | |
| 7,427,654 B1 | 9/2008 | Cheng | |
| 7,514,528 B2 | 4/2009 | Kauffman | |
| 7,691,923 B2 | 4/2010 | Lundquist | |
| 7,799,943 B2 | 9/2010 | Shah | |
| 7,985,809 B2 | 7/2011 | Krawczyk | |
| 2007/0299155 A1 | 12/2007 | Carpenter | |
| 2009/0285896 A1 | 11/2009 | Bezwada | |

OTHER PUBLICATIONS

USPTO structure search, Oct. 2014.*
Sury and Hoffman, Helv. Chim. Acta 26, 1815(1953).
Mariella et. al. JOC, 20, 1702(1955).
Adamcik and Miklasiewicz, JOC 28, 336(1963).
Furthermore, Choi et. al. Bull. Korean Chem. Soc. 1996, vol. 17,No. 4 p. 395.

* cited by examiner

*Primary Examiner* — Gregory Listvoyb

(57) ABSTRACT

The Michael reaction is employed, for example, to condense methyl acrylate with diethyl malonate to prepare the corresponding tetra-ester. Subsequent reaction with primary amines followed by thermal condensation results in spiroimides. A similar series of reaction steps can be performed starting with malonamides.

16 Claims, No Drawings

AMIDE-IMIDE COMPOUNDS AND THEIR CORRESPONDING POLYMERS

This application claims the benefit of U.S. Provisional Patent Application Ser. No. 61/688,100 filed May 8, 2012.

TECHNICAL FIELD AND BACKGROUND

The present invention relates to unique amide and imide containing compounds and polymers, useful as plastics, coatings and cosmetic ingredients or pharmaceutical excipients, as non-permanent degradable plastics for environmental or medical applications, film formers, tackifiers, tablet binders, haircare fixatives and conditioners, and so forth. Non-polymeric compounds can also have a variety of other uses; for example, high temperature heat transfer or hydraulic fluids, unctuous cosmetic bases, hair care conditioners, surfactants, and solvents to name a few.

Because these amide, and/or imide compounds are large molecules with high boiling points, they are believed to be of low skin and eye toxicity. This makes them of importance especially to the cosmetic and the pharmaceutical industries.

I have found that the Michael reaction of acrylate esters and dialkyl malonates or N,N'-dialkyl malonamides proceeds to produce a tetra-ester or diester diamide suitable for further reaction with mono functional primary amines and/or di-functional chain extenders such as alkanolamines and diamines, affording inexpensive polymers for said applications.

When said polymers are prepared from alkanolamines and said tetracarboxylates, or diamide diesters, the resulting polyesteramide or polyesterimide/amide polymers will eventually hydrolyzed in aqueous solutions. The degradable polymers so formed are inexpensive, valuable, novel and not anticipated by the prior art.

PRIOR ART 1,3,3,5-pentanetetracarboxylic acid and it's esters were first described by Wiest, U.S. Pat. No. 2,396,626 (Mar. 12, 1946). In his example 8, he shows that diethyl malonate will react with methyl acrylate by the Michael reaction to form said tetraester. Several supposed improvements are described in subsequent patents to Sabahi et. al., U.S. Pat. Nos. 5,347,043; 5,350,875; 5,399,279; 5,430,177; 5,536,872; 5,538,661; 5,569,779 and 5,683,618. These patents describe improved catalysts for this Michael reaction and uses for the said tetracarboxylates or polycarboxylate derivatives of malonates and acrylate esters.

Lincoln and Drewitt, U.S. Pat. No. 2,502,576 (Apr. 4, 1950) recognized that certain tetracarboxylates when reacted with primary diamines would form polyamideimides. They mention 1,3,3,5-pentanetetracarboxylic acids and claim that when reacted with primary diamines, looses carbon dioxide to form 1,3,5-pentanetricarboxylic acid in-situ. This tri-acid then condenses with said diamine to afford polyamides containing glutarimide rings. If the ester of said tetracarboxylic acid is used in the same reaction then carbon dioxide is not eliminated and a different product is obtained. No further details of this other product are revealed. Subsequent patents that reference this patent do not reveal anything to shed light on said product formed from said tetracarboxylate. The reaction of diamines with tetracarboxylic acids especially with the corresponding anhydrides is well documented (for example, Cheng et. al. U.S. Pat. No. 7,427,654: Sep. 24, 2008); however, no other patents illustrate how to use said tetraesters such as tetramethyl 1,3,3,5-pentanetetracarboxylate to prepare polyamideimide polymers with useful properties.

Frosch, U.S. Pat. No. 2,386,454 (Oct. 9, 1945) and Kropa, U.S. Pat. No. 2,463,977 (Mar. 8, 1949) appear to be the earliest references for preparing polyesteramides from for example, ethanolamine and dicarboxylic acids or esters. Dayton, U.S. Pat. No. 2,806,822 (Sep. 17, 1957) shows how to add reactive unsaturation to said polymers. Shalaby et. al. U.S. Pat. No. 4,209,607 prepare said polymers by pre-forming a bis-oxamidodiol and condensing it with a di-acid. Barrows, U.S. Pat. No. 4,343,931 (Aug. 10, 1982) in a similar reaction condenses lactic or glycolic acid with a diamine resulting in a compound containing diol and diamide. Many other variations are known such as those found in U.S. Pat. Nos. 4,380,622; 4,483,975; 4,536,563; 4,604,449; 4,855,397; 5,644,020; 5,902,875; 6,268,465; 7,166,680; 7,196,127; 2007/0299155 and 2009/0285896. This list is not meant to be exhaustive as the polyesteramide patent literature is extensive.

A number of patents have issued to the Rohm and Haas company which describe the use of malonamide derivatives as part of a Michael reaction, the malonamide being the Michael donor. This reaction is between a Michael donor and a Michael acceptor both functionalities being incorporated in the same or different polymers and or cross linkers. Examples of these patents are Krawczyk et. al.; U.S. Pat. No. 7,985,809 (Jul. 26, 2011); Lundquist et. al.; U.S. Pat. No. 7,691,923 (Apr. 6, 2010); Shah et. al.; U.S. Pat. No. 7,799,943 (Sep. 21, 2010); Kauffman et. al.; U.S. Pat. No. 7,514,528 (Apr. 7, 2009); Beckley et. al.; U.S. Pat. No. 7,396,429 (Jul. 8, 2008); amongst others. The earliest patent to this type of chemistry is Haarlem; U.S. Pat. No. 4,602,061. It shows how cross linkers like trimthylol propane triacrylate will cure polymers containing malonate groups.

Spiro-bis-imides are known compounds and can be readily prepared by first condensing acrylonitrile with diethyl malonates and then treating the resulting 1,5 dicyano-3,3-diethyl-pentanedicarboxylate with a strong mineral acid like HCL (Sury and Hoffman, Helv. Chim. Acta, 26, 1815(1953); Mariella et. al. JOC, 20, 1702(1955), and Adamcik and Miklasiewicz, JOC, 28, 336(1963)). Furthermore, Choi et. al., (Bull. Korean Chem. Soc. 1996, Vol 17, No. 4 p. 395) afford procedures for the synthesis of N-alkyl derivatives of said spiro-bis-imides by alkylating the anion of the acidic imide.

SUMMARY

A process for preparing a variety of spiroimide containing compounds comprising;
  a.) mixing a primary amine or amines, a catalyst, and a tetra-alkyl 1,3,3,5 pentanetetracaboxylate,
  b.) heating said mixture under a pure nitrogen sweep to a temperature of 125-170 C, and
  c.) removing volatile alcohols by first atmospheric then vacuum distillation until a desired conversion is achieved then,
  d.) optionally neutralizing or removing said catalyst.

The above process wherein the primary amine or mixtures of said amines have the following structure;
  a.) H2N—R-T, Where R=an aliphatic chain of 1-20 carbon atoms, or an aromatic group and both are optionally substituted with aromatic, heterocyclic, nitrogen, oxygen, halide, silicone, phosphorus containing groups or combinations of said groups, and T=—H or —NH2, or —OH;
  b.) or combinations of such compounds wherein the compounds containing di-primary amines, or primary alkanolamine, or mixtures of both types, make up 90 to 100% of said amines.

The above process wherein said catalyst is selected from the alkoxides of sodium, or potassium, or titanium, or strong amines such as DABCO.

The above process wherein said catalyst is used at 0.1 weight % to 5 weight % of said reaction mixture.

The above process wherein said catalyst is optionally neutralized or removed at the end of said reaction with a mineral acid such as hydrochloric acid, or sulfuric acid, or aliphatic acids such as acetic acid, or acidic ion-exchange resins such as Amberlyst 15

The above process of wherein the alkanolamine has the following structure; HO—(CHR)x(CHR')x-NH2 where R and R'=C1-8 alkyl chain optionally substituted with aromatic, or heterocyclic, or silane, or nitrogen, or oxygen, or halogen, or silicone, or phosphorus containing groups or combinations of said groups, and x=1-20 carbon atoms.

The above process wherein the products of said process contain combinations of amide, or imide, or carboxylate ester or acid functionality.

The above process wherein the product is a polymer containing a combination of amide, imide and ester groups.

A polyamide-co-imide polymer containing at least 1 weight % of the following structure in said polymer's backbone;

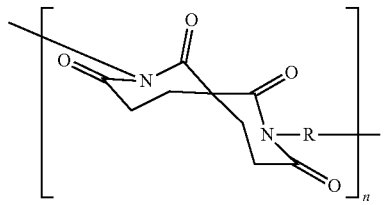

wherein R is the organic residue of a primary diamine and said primary diamine is of the following structure;
H2N—R—NH2 where R is a alkyl radical containing 1-20 carbon atoms or an aromatic, or polyaromatic in which said R can also be optionally substituted with heterocyclic, oxygen, nitrogen, silicone, halide, and/or phosphorus containing groups.

A polyamido-co-imide-co-ester polymer containing at least 1 weight % of the following structure in said polymer's backbone;

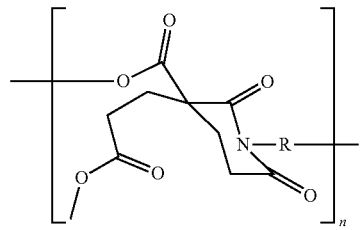

A compound of the following structure;

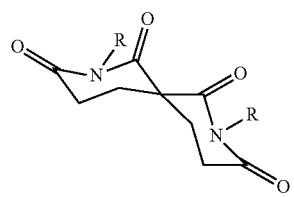

wherein R is primary amine, or said alkanolamine, or (R)₂N—R'—NH2 where R is hydrogen or a C1-6 alkyl radical and R' is a C2-10 alkyl di-radical, or mixtures of said amines.

A process for preparing a variety of spiro-imide containing compounds comprising;

a.) mixing a primary amine or amines with a dialkyl malonate to form the corresponding mono and/or disubstituted malonamide, b.) heating said pre-formed malonamide under a pure nitrogen sweep to a effective temperature in the range of 50-150 C, reacting two or more moles of a Michael receptor acrylate to form the corresponding diamide diester compound, then c.) optionally adding said primary diamine or said alkanolamine or mixtures of each and, c.) removing volatile alcohols by first atmospheric then vacuum distillation until a desired conversion is achieved then, d.) optionally neutralizing or removing said catalyst.

DETAILED DESCRIPTION

I have found that diethyl malonate will react with a slight excess of methyl acrylate neat to form crystalline 3,3-diethyl-1,5-dimethyl pentanetetracarboxylate in nearly 100% yield. This exothermic reaction is conducted by slowly adding (a small) excess of MA to diethyl malonate containing a catalytic amount of sodium methylate at <50 C. The reaction is finished by vacuum stripping the small excess of methyl acrylate. Other acrylate esters can be used but the methyl ester affords a crystalline adduct that can be purified if necessary by recrystallization; however, I have found that said crystalline adduct can be left to crystallize at lower temperatures and the small amount of non-crystalline liquid adducts can be simply decanted leaving suitably pure said adduct, suitable for subsequent reactions with primary amines, diamines and alkanolamines. This Michael reaction doesn't employ solvents and is remarkably easy to perform. Using readily available raw materials, this simple exothermic reaction can be performed industrially at low cost.

Subsequent reaction with primary diamines, and/or alkanolamines does require high temperatures in the 125-170 C range. Initially said crystalline adduct is melted under a nitrogen sweep, charged with a catalytic amount of sodium methylate, and heated to 125-170 C. Said amine is slowly added. This can be done under a reflux condenser. At some temperature in the 125-170 C or even higher, alcohol reflux will begin. As the condensation proceeds, the reflux will cool the reaction to a lower temperature of 130-150 C or so. At this point, the reflux is changed to a distillation. The amine addition is slowly continued with the goal of maximizing the formation of a diamide-diester. The temperature must not be allowed to rise above 140-160 C or so because above these temperature color will increase unacceptably. It is also important to maintain a pure nitrogen sweep in order to further minimize color formation. When alcohol distillation slows, vacuum can be applied at the best level available. The reaction is maintained under vacuum until the viscosity is in the desired range. This must be determined experimentally. Infrared analysis is very useful in following conversion especially with the alkanolamines by disappearance of OH absorption.

In an alternative approach to the same reaction, the primary amine, or diamine, and/or alkanolamine can be mixed with the tetra-ester at room temperature. There is a modest exotherm and the mixture is aged for at least 24 hours. With a pure nitrogen sweep, it is heated to an optimum temperature usually in the 125-170 C or more likely 130-150 C. The reaction is then conducted as above, and the distillate is collected and eventually the reaction is placed under vacuum.

However, in both of the above cases, if the temperature is slowly increased even up to 250 C at atmospheric pressure. At some temperature in the 200-250 C range, a rapid reaction takes place generating vigorous boiling and rapid distillation of volatiles. This reaction is the rapid conversion of amide to imide and subsequent distillation of alcohols. The mixture now placed under best vacuum is again heated to 200-250 C where vigorous boiling takes place as the remaining amide is converted to imide. Now unless one uses a dry ice trap, the low by alcohols are removed as a gas and not trapped. When the boiling slows, the formation of imide has slowed. Infrared analysis can be used to indicate the conversion to imide by disappearance of the 1550-1500 absorption. When judged complete, the mixture is cooled to a lower temperature and discharged from the reactor. The problem with high temperature is the resulting very dark color usually a very deep reddish brown. Only when these condensations are performed at lower temperatures is the color reduced. If the product, a spiro-diimide is distillable or can be recrystallized, then the higher temperature reaction would be desirable.

The reaction steps can be illustrated as follows:

As can be seen, any one of the three amide possibilities will afford the spiro-bicyclodiimide. Formation of tri- and tetra-amides or unreacted starting tertraester is statistically possible but is minor and does not detract from the utility of said embodiments.

Judging from the MW of the alcohols that initially distill over at atmospheric, being closer to the MW of ethanol, suggests that the initial amides form from the ethyl esters. This would be expected, because by the inductive effect, as they are more electron deficient.

Realistically, the conversion to imide is not complete, hence the condensates are mixtures of amide and imide with residual ester groups.

Dialkyl malonates such as diethyl malonate react with primary amines to form N,N'-dialkyl malonamides, which can be crystalline compounds. Said crystalline compounds can be purified by recrystallization. The purer dialkyl malonamides can then undergo the Michael reaction with two moles of alkyl acrylate to form a single product. Such a purer Michael condensate can react with di or poly functional amines or alkanolamides to generate polymers with potentially fewer byproducts. For example:

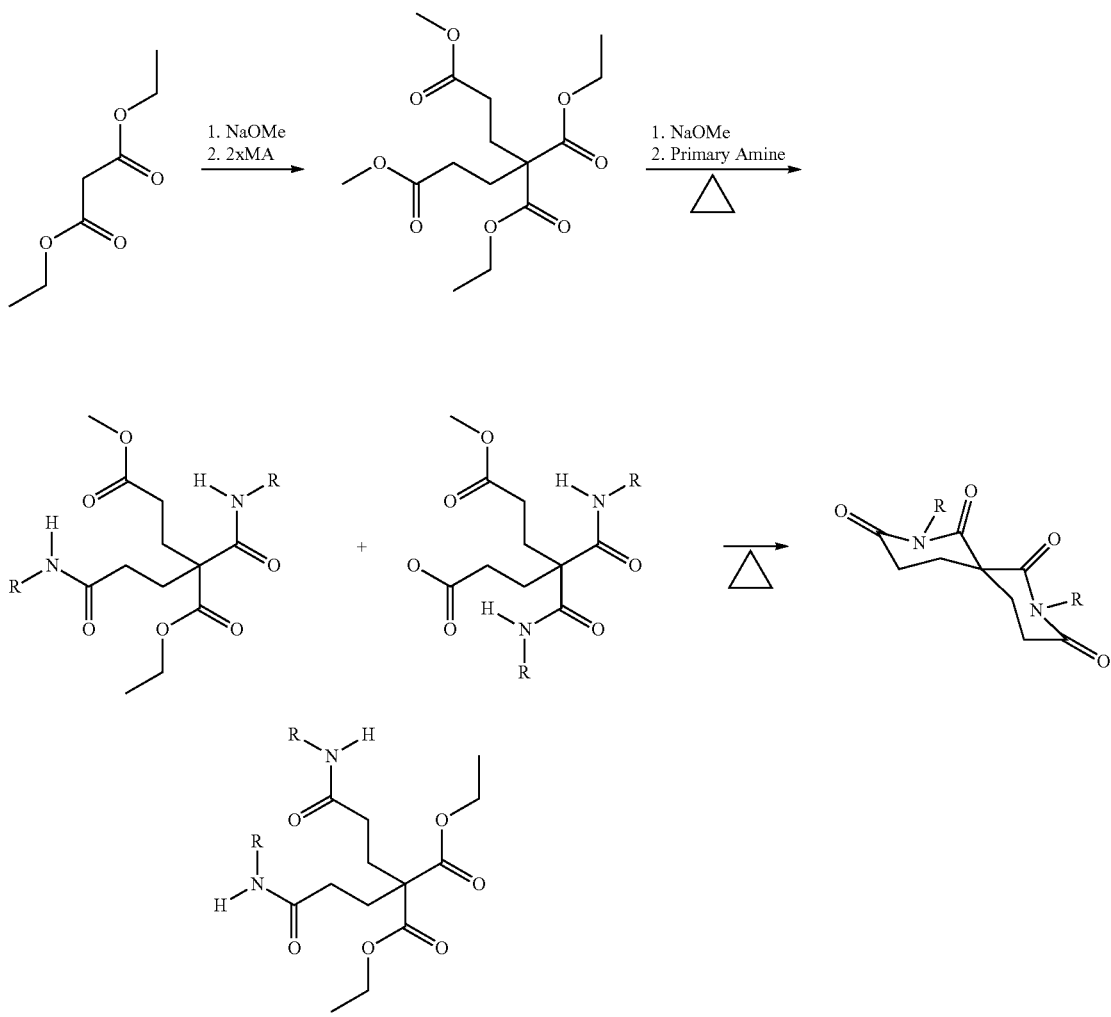

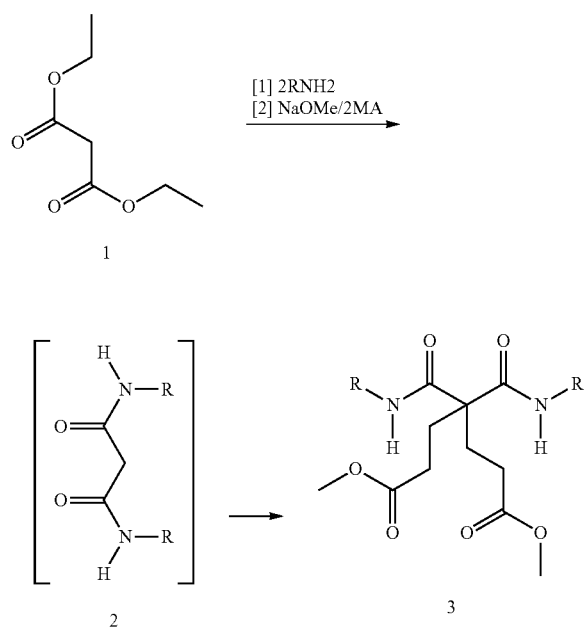

Primary amines will form amides when simply mixed with said tetracarboxylate even at room temperature. This amonolysis takes much longer than the higher temperature one described above but is simple and easily accomplished. The product usually formed after several days can be heated under a nitrogen sweep to effect removal of alcohols and conversion to imide as described above. Likewise, said amines can be mixed with diethyl malonate at RT to form diamides. Those prepared from methylamine and octylamine, for example, are crystalline compounds.

If the R groups are connected together, then a polyimide will result. Such spiro containing polyimides would be expected to exhibit unique properties. The spiro group will increase the rigidity of the polymer chains increasing the Tg of the polymer and increasing tensil strength. Incorporation of said spiro monomers in nylon based polyamides results in more easily processed polymers by lowering their mp. The spiro group disrupts nylon crystallinity hence lower mp's.

The components of the Spiro or spiroamide or amide-imide or amide-ester or imide-ester or any combination of said functional groups can be incorporated as components of co- or terpolymers. For example, nylon 6,6 can be prepared with useful amounts of said functionalities. Numerous condensation polymers can benefit from the incorporation of said groups, generating polymers with unique properties.

The infrared spectrums are listed in table 1 according to major absorptions (uncorrected):

The fact that there are two carbonyl absorptions with the lower frequency one being more intense is a hallmark of cyclic imides. The spectra also reveal a band around 1500-1550 cm-1. This absorption is secondary amide because the reaction forming imide is not expected to be complete especially when purification is not an option. The band however is small and shows that the imide is by far the major component. The absorptions around 3400 cm-1 shows up in the N-ethyl succinimide spectra as it does in said compounds and is most likely residual amide.

However, when the same reaction sequence is carried out with the preformed and purified N,N'-dialkyl malonamides the absorption at 1550-1500 is significantly reduced. Employing the N,N'-dimethylmalonamide, a crytalline purified starting material condensed with MA and reacted with the above said reaction conditions, affords the same crystalline product with an identical IR spectrum. The H-NMR spectrum reveals a somewhat unexpected result, in that only two protons instead of four are found around 2 ppm. This is because only one methylene is not in one of the carbonyls deshielding cones. This can be readily seen with actual physical models.

An IR spectrum of a said malonamide DMAPA starting material is illustrated for comparison. The absorption at 1550-1500 is very intense as expected; however the reaction products from the high temperature reaction results in a purer imide derivative.

EMBODIMENTS

Obviously other primary amine and diamines can be employed. The list of such amines is extensive and well known to those of ordinary skill in the art.

However alkanolamines of various structures can also be employed to prepare polyesteramides (or mixed amide/imide). Thus ethanolamine will react with said tetra-ester adduct to afford such polymers. Polyamide-co-esters so prepared by partial amidation can be hydrolyzed in aqueous base to afford polycarboxylate salts without hydrolyzing the amide functionality. This results in water soluble or dispersible polyamides with anionic carboxylate functionality.

Alkanolamines can be employed to form diol terminated spiroimides. These can be used to form a wade variety of polyesters containing spiroimides. Likewise, diamines can be employed to form diamino terminated spiroimides for use as comonomers for incorporation into polyamides such as nylon.

TABLE 1

| Spectral data | |
|---|---|
| Reaction sequence: | absorptions(m = medium, s = strong, vs = very strong) cm−1 |
| tetraester + octylamine: | 2900s, 2800s, 1720s, 1650vs, 1520m, 1300s, 1150m, 1120m |
| DEM + octylamine then MA: | 2900vs, 2800s, 1720m, 1650s, 1450s, 1350m, 1150m, 1120m |
| DMAPA + DEM: | 3400s, 2900s, 2750s, 1650vs, 1550vs, 1300s |
| DMAPA + DEM then MA: | 2900s, 2800s, 1720s, 1650vs, 1450m, 1350s, 1200m, 1140m |
| Methylamine + DEM then MA: | 2900m, 1720s, 1650vs, 1500m, 1350s, 1300s, 1100s |
| Methylamine + DEM then MA NMR, d6DMSO: | 1.9m(2), 2.6m(6), 3.0s(6) |

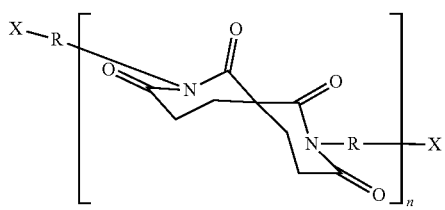

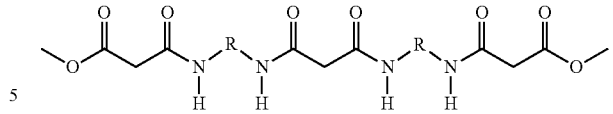

Where X=—OH or NH2 or tertiary amine or tertiary amine derivatives and R is an alkyl group etc.

The previously mentioned spiro-bis-imide can be prepared from ammonia itself. It can react with said tetra-ester adduct to form a spiro bis-imide that can react through the imide N—H groups for example with formaldehyde or epichlorohydrin resulting in unique spiro polymers.

If the bis-adduct of preformed malonamide is not heated as above to form the spiro-imide but instead is allowed to undergo lower temperature amonolysis then a new tetra-amide results. For example, N,N dimethylpropylamine will afford bis tertiary amine compounds that can be quaternised with either mono alkylating agents such as alkylhalides, benzyl chloride, epoxides and so forth or dialkylating agents such as epichlorohydrin or dichloroalkanes and so forth resulting in quaternaries or polyquaternaries. This is illustrated with DMAPA bis-malonamide then reacted with HMDA, below:

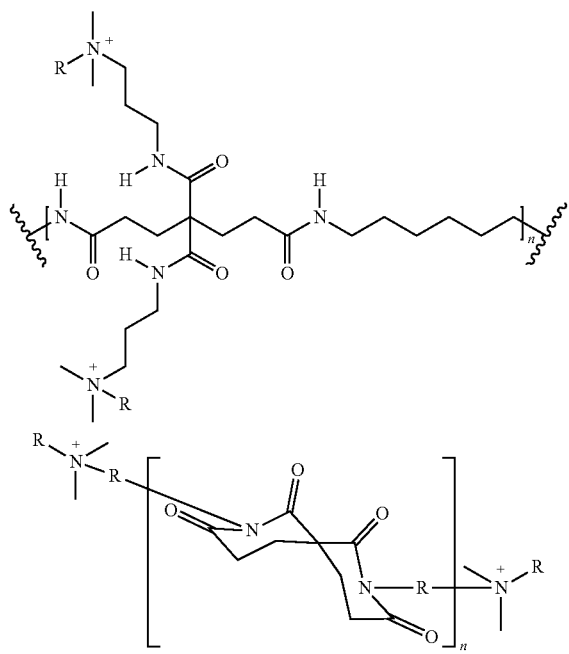

Should the spiro-imide be desired then the higher temperature reaction is employed and DMAPA can be quaternized with a variety of alkylating agents as illustrated above.

In a similar vein, various diamines or combinations of diamines can be condensed with DEM or other malonates so that a preliminary malonate ester terminates the compound; for example:

This intermediate can be synthesized with excess DEM and both the excess DEM and resulting alcohol can be removed after the reaction. The Michael reaction can then be conducted followed by thermal conversion to the spiro structure. The intermediate can be oligomeric with several repeating units as long as it terminates in ester groups.

Although the reaction of various primary amines with DEM affords crystalline products that can be readily purified, the resulting amides are not as potent facilitators of the Michael reaction as are the malonate esters. The reason being that the esters can resonance stabilize the malonate anion and can also promote ionization by the inductive effect. The amides however have a nitrogen atom that can share its electrons with the amide oxygen reducing the ability of the amide to stabilize the malonate anion by resonance; therefore, the malonamides are not as active in the Michael reaction and require more catalyst and temperature to condense with acrylates.

The above malonate terminated monomers contain esters and amides and are more reactive towards acrylates. After the Michael reaction, subsequent thermal conversion to spiroimide structures along with amide and ester groups can occur. Furthermore, reaction with primary diamines such as HMDA results in polymers. The monomers can react with other primary diamines along with other diesters to form co- or terpolymers.

EXPERIMENTAL

Abbreviations: MA=methyl acrylate, DEM=diethyl malonate, HMDA=hexamethyldiamine, DMAPA=N,N-dimethylpropylamine, Diadduct=said tetracarboxylate.

Equipment:

All IR's were obtained on a Perkin-Elmer model 1310, GC analysis were performed on a HP5890 with TC detectors.

Example 1

Reaction of DEM with MA (Synthesis of the Diadduct)

A three neck one liter round bottom flask equipped with a thermometer, condenser, dropping funnel and mechanical stirrer was charged with 338 g of DEM. The pressure equalizing funnel was charged with 363 g MA and 1.5 g 25% NaOMe was added with stirring to the DEM charge while a slow stream of N2 was passed over the pot charge and continued for the rest of the reaction. The pot charge was heated until 40-50 C then turned off, and then the MA charge was added drop-wise. If the temperature went above 60 C because of the exotherm, the mixture was cooled in an ice bath to keep the temperature below 60 C. If necessary the MA feed can be reduced or temporarily turned off. The goal is to optimize the generation of the di-adduct by not employing an excess of MA. Once the MA is added, the mixture is allowed to stir at ambient temperatures for one hour. Then it is heated to 85-95 C for one hour. Finally, vacuum stripping at 85-95 C and −25"Hg until distillate stops (usually very little if any distillate comes over). The product, a clear colorless liquid that crystallizes upon cooling to form large crystals and a small amount of liquid. The liquid can be decanted and the crystalline product (mp 25-30 C, MW 332) can be used in subsequent reactions as is. GC analysis shows that the crystalline product is mostly di-adduct (>90%). The decanted liquid is mostly mono-adduct, some unreacted DEM and di-adduct. The yield of diadduct is approximately 80-90%. The diadduct (catalyst must be neutralized, however to avoid ester interchange) can be recrystallized from methanol (mp-26-28 C).

If excess MA is used in this reaction, it forms small chains because the anion formed during the Michael reaction can react with excess MA before it reacts with the malonate anion. Another precaution is to conduct the Michael reaction at lower temperatures to also eliminate this side reaction.

Example 2

Reaction of the Above Diadduct with Primary Amines

A.) Reaction of Diadduct with HMDA.

To a three neck 250 ml round bottom flask equipped with mechanical stirrer, pressure equalizing dropping funnel, thermometer, and condenser, was charged with 135 g (0.4 moles) of the above melted diadduct. Under a slow N2 sweep 46.4 g (0.4 moles) of HMDA are added drop-wise as the temperature is raised to 135-145 C. The HMDA addition is completed at this temperature and the reaction is changed from reflux to distillation. The temperature is raised slowly to no more than 150-180 C collecting distillate until it slows then evacuating to −25"Hg. The mixture thickens until stirring becomes a problem at which point it is discharged as a viscous liquid. Upon cooling, a lightly colored (Gardner 2-3) flexible plastic results. Infrared analysis reveals major absorptions at 1720, 1650 but smaller at 1525 CM-1. If a sample is dissolved in DMSO and heated on a hot plate at 200 C, with time the peak at 1525 is reduced indicating formation of imide. The resulting polymer is a mixture of spiroimide, imide, and amide functionalities.

b.) Reaction with Octylamine:

Using identical equipment, 88 g (0.265 moles) of the melted di-adduct was charged. Under a N2 sweep, 68.5 g (0.53 moles) octylamine was added drop-wise while the temperature was raised slowly to 165 C at which point all was added and the mixture was refluxing. The reaction was switched to distillation and volatiles were removed as the temperature was raised slowly to 225 C at which point violent boiling occurred with rapid distillation. After this stage, the reaction was placed under −25"Hg vacuum to remove residual volatiles. It was then cooled and discharged as a tannish oil. Collected 105 g with several grams left in reactor, theoretical yield is 119.5 g.

Infrared analysis reveals major absorptions at 1720 and 1650 CM-1 but reduced peaks at 1520. Distillation at highest vacuum (<10 mmHg estimated) resulted in a viscous oil bp >250 C.

c.) Reaction with Methylamine:

In the same equipment was charged 92.9 (0.28 moles) of melted diadduct along with 43.5 g (0.56 moles) of 40% aqueous methyl amine. The mixture became homogeneous as amonolysis proceeded with a modest exotherm. The mixture was left at ambient over night. It was then heated under an N2 sweep up to 140 C to remove volatiles. Heating was continued up to 250 C and the −25"Hg vacuum. Cooling and discharge resulted in 66 g of a tan oil (theoretical solids are 68.8 g). Upon standing at RT, crystals formed which were separated and recrystallized from methanol affording needles mp 154-155 C. The infrared spectrum of these crystals, clearly indicate substantial spiroimide formation.

d.) Reaction with Ethanolamine:

Ethanolamine was mixed with the melted diadduct at ambient on a 1:1 molar basis. A slight exotherm was observed and the mixture was left to react overnight. In the same equipment set-up for distillation, 190 g of this clear colorless mixture under a N2 sweep, was heated slowly to 140 C while collecting distillate. When distillate production slowed, the mixture was placed under −25"Hg for several hours at no more than 150 C. When stirring became difficult, the very viscous liquid was discharged.

In the EA reaction, experience shows that raising the temperature higher than 150 C results in excessive color but faster more complete reaction. However, not as much imide is produced at lower temperatures; therefore, a polyester-amide-imide results. The above product upon cooling is a slightly tacky brittle polymer. Holding the reaction under vacuum at 150 C for longer durations results in higher MW polymers.

A sample of this polymer was mixed with water and after several hours a partial hydrolysis had occurred. A residual oil remained believed to be amide and or imide residues.

e.) Reaction with a Mixture of EA and HMDA:

Both EA and HMDA (both at 0.25 moles or 1 eg.) were added to the melted diadduct at RT and left overnight. Next day, this mixture were heated and stirred in the same equipment as above. As it warmed, 0.2 g of 25% NaOMe were added. Distillation at atmospheric continued to 150 C until it slowed. It was then placed under vacuum (−25"Hg) until its viscosity increased to where stirring was problematic, then discharged. The resulting light colored plastic was slightly tacky but flexible. In all of the above reactions, the diadduct was used as is with the liquid phase decanted off and the catalyst unneutralized.

Example 3

Preliminary Reactions of Primary Amines with DEM Followed by the Michael Reaction with MA General Procedure:

A suitable Erlenmeyer flask was charged with 1 mole of DEM. Two moles of a primary amine were added with stirring, resulting in a modest exotherm and if heterogeneous, clearing usually within one hour. The mixture is left to stand at RT for 24 hrs and can form a solid mass in that time. The solid crystalline mass is recrystallized from methanol.

| Amine | % yield (after recrystallization) | MP Comments |
|---|---|---|
| a.) Methylamine: | 63 | 134-135 C. |
| b.) Octylamine: | 85 | very high bp wax |
| c.) DMAPA: | liquid | viscous high bp liquid |
| d.) EA: | 61 | |
| e.) HMDA | oligomeric | |

Subsequent Reaction of the Above with MA:

If crystalline, it is added to NMP usually at 50% solids to dissolve by heating, to 50-100 C if necessary, under a N2 sweep. When dissolved, 0.1-0.5% 25% NaOMe is added with stirring, and upon catalyst addition, a noticeable but modest color change occurs. From experience, this color change indicates an active catalyzed mixture. If necessary the mixture is cooled to 50-60 C and 2.1 moles of MA are added drop wise while maintaining the temperature in the 50-60 C range by cooling or MA addition rate. If the exotherm slows or stops, it is because not enough catalyst remains in the mixture, more can be added to re-catalyze the reaction. Once MA addition is finished, the mixture is held at 60 C for one hour then the temperature is slowly raised over another hour until distillation begins. The distillate is monitored by GC(HP-1 30 m column at 100 C, injector 175 C and TC detector at 225 C) for methanol and MA. If too much MA is coming over, then the Michael reaction was not given enough time to complete and it should be added back to the reaction mixture to react out. When GC analysis indicates that little MA is in the alcohol distillate, the reaction is over. When satisfied that as much MA has reacted as possible, then the distillation is continued and results in producing two moles of methanol. The mixture is heated slowly to maintain methanol production as measured by the distillation temperature in the 60-75 C range. When the temperature rises above 170 C and the overhead distillate temperature goes above 75-80 C, then NMP is starting to distill. A small aliquot of the NMP mixture can be added to water where the product is insoluble and precipitates out of solution. It can be recovered, weighed and analyzed quickly by IR. If too much 1525-1550 CM-1 absorption is observed, the reaction can be cooled to 140-160 C and held there until completion as gauged by the further IR analysis. The mixture is then vacuum distilled to remove NMP until a concentration and temperature is reacted where the product is still soluble. It is then discharged from the reactor where it can cool, crystallize and be recovered. If not crystalline, then the NMP can be removed and the resulting liquid recovered an optionally purified by vacuum distillation.

Methylamine afforded a crystalline product identical to that prepared from the di-adduct. DMAPA afforded an oil that was vacuum distilled at very high temperature(<10mmHg, 250C). EA and HMDA afforded polymers.

I claim:

1. A process for preparing a variety of spiroimide containing compounds comprising;
    a.) mixing a primary amine or amines and tetra-alkyl 1,3,3,5 pentanetetracarboxylate,
    b.) heating said mixture under a pure nitrogen sweep to a temperature of 125-170 C, an
    c.) removing volatile alcohols by first atmospheric then vacuum distillation until a desired conversion is achieved then,
    d.) optionally neutralizing or removing said catalyst.
2. The process of claim 1 wherein the primary amine or mixtures of said amines have the following structure;
    a.) H2N—R-T, Where R=an aliphatic chain of 1-20 carbon atoms, or an aromatic group and both are optionally substituted with aromatic, heterocyclic, nitrogen, oxygen, halide, silicone, phosphorus containing groups or combinations of said groups, and T=—H or —NH2, or —OH;
    b.) or combinations of such said amines wherein the compounds
containing di-primary amines, or primary alkanolamine, or mixtures of both types, make up 90 to 100% of said amines.
3. The process of claim 1 wherein said catalyst is selected from the alkoxides of sodium, or potassium, or titanium, or strong amines such as DABCO.
4. The process of claim 1 wherein said catalyst is used at 0.1 weight % to 5 weight % of said reaction mixture.
5. The process of claim one wherein said catalyst is optionally neutralized or removed at the end of said reaction with a mineral acid such as hydrochloric acid, removed at the end of said reaction with a mineral acid such as hydrochloric acid, or sulfuric acid, or aliphatic acids such as acetic acid, or acidic ion-exchange resins such as Amberlyst 15.
6. The process of claim 1 wherein the alkanolamine has the following structure; HO—(CHR)x(CHR')x-NH2 where R and R'=C1-8 alkyl chain optionally substituted with aromatic, or heterocyclic, or silane, or nitrogen, or oxygen, or halogen, or silicone, or phosphorus containing groups or combinations of said groups, and x=1-20 carbon atoms.
7. The process of claim 1 wherein the products of said process contain amide, or imide, or carboxylate esters or acids functionality, or combinations of said functional groups.
8. The process of claim 1 wherein the product is a polymer containing said functional groups.
9. A polyamide-co-imide polymer containing at least 1 weight % of the following structure in said polymer's backbone;

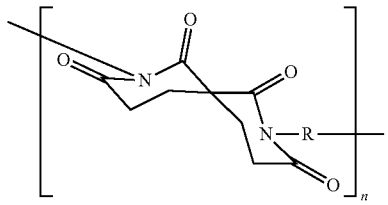

wherein R is the organic residue of a primary diamine and said primary diamine is of the following structure;
H2N—R—NH2 where R is a alkyl radical containing 1-20 carbon atoms or an aromatic, or polyaromatic in which said R can also be optionally substituted with heterocyclic, oxygen, nitrogen, silicone, halide, and/or phosphorus containing groups.
10. A polyamido-co-imide-co-ester polymer containing at least 1 weight % of the following structure in said polymer's backbone;

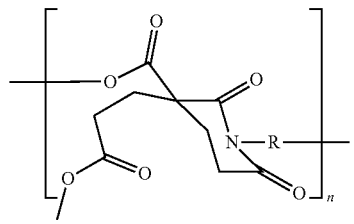

11. A compound of the following structure;

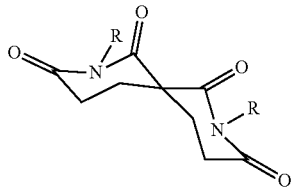

wherein R is the radical of said primary amine, or mixture of said amines, or said alkanolamine, or (R")2N—R'—NH2 where R" is a C1-6 alkyl radical and R' is a C2-10 alkyl diradical.
12. A process for preparing a variety of spiroimide containing compounds comprising;

a.) mixing a primary amine or amines with a dialkyl malonate to form the corresponding mono and/or disubstituted malonamide, b.) adding a catalyst to said mixture, and optionally a solvent, and c.) heating said pre-formed malonamide under a pure nitrogen sweep to a effective temperature in the range of 50-150 C, and reacting two or more moles of a Michael receptor acrylate to form the corresponding diamide diester compound and d.) optionally adding said primary alkyl or diamine or said alkanolamine or mixtures of each and, e.) removing volatile alcohols by first atmospheric then vacuum distillation until a desired conversion is achieved then, f.) optionally neutralizing or removing said catalyst.

13. The process of claim 12 wherein the catalyst is said alkoxide.

14. The process of claim 12 wherein the solvent is water soluble and boils above 140 C.

15. The process of claim 14 wherein the solvent is NMP, or DMF, or DMSO.

16. The process of claim 12 wherein the acrylate ester is a C1-C6 alkyl ester.

* * * * *